United States Patent [19]

Zagury et al.

[11] Patent Number: 6,093,405
[45] Date of Patent: Jul. 25, 2000

[54] INACTIVE BUT IMMUNOGENIC CYTOKINES, PHARMACEUTICAL COMPOSITIONS CONTAINING SAME, AND METHODS OF TREATING HOMEOSTATIC DISORDERS ASSOCIATED WITH AN OVERPRODUCTION OF CYTOKINES

[75] Inventors: Daniel Zagury; Jean-François Zagury, both of Paris; Bernard Bizzini, Le Mesnil-Saint-Denis, all of France

[73] Assignee: Neovacs, Paris, France

[21] Appl. No.: 08/167,867

[22] PCT Filed: Jun. 17, 1992

[86] PCT No.: PCT/FR92/00544

§ 371 Date: Jun. 27, 1994

§ 102(e) Date: Jun. 27, 1994

[87] PCT Pub. No.: WO92/22577

PCT Pub. Date: Dec. 23, 1992

[30] Foreign Application Priority Data

Jun. 17, 1991 [FR] France .................. 91 07399

[51] Int. Cl.⁷ .............. A61K 39/00; A61K 39/395; A61K 45/05
[52] U.S. Cl. ............. 424/198.1; 424/184.1; 424/145.1; 424/85.1
[58] Field of Search .................. 530/300, 345, 530/350, 351, 402, 403; 424/198.1

[56] References Cited

PUBLICATIONS

Erb et al., 1997, J. Exp. Med. 185(2):329–339.
Elliott et al., 1997, Brit. J. Rheumatol. 36(5):589–593.
Probert et al., 1995, Proc. Natl. Acad. Sci. USA 92(24):11294–11298.
Webb et al., 1998, Lab. Invest. 78(8):939–948.
Belardelli, F., 1995, APMIS 163:161–179.
Stein et al., 1993, Clin. Infect. Dis. 17:749–771.
Barr et al., 1991, Molec. Biochem. Parasit. 45:159–170.
Marcucci et al., 1986, Biochem. Biophys. Res. Comm. 134:1412–1418.
White et al., 1990, Biol. 18:271–280.

*Primary Examiner*—Frank C. Eisenschenk
*Assistant Examiner*—Jeffrey S. Parkin
*Attorney, Agent, or Firm*—Browdy and Neimark

[57] ABSTRACT

Cytokines, which are biologically inactive in humans but remain immunogenic, are used in pharmaceutical compositions to promote a neutralizing immune response against native cytokines when administered to a subject in need thereof to treat homeostatic conditions and disorders associated with an overproduction of cytokines.

12 Claims, No Drawings

INACTIVE BUT IMMUNOGENIC CYTOKINES, PHARMACEUTICAL COMPOSITIONS CONTAINING SAME, AND METHODS OF TREATING HOMEOSTATIC DISORDERS ASSOCIATED WITH AN OVERPRODUCTION OF CYTOKINES

This application is a National Stage application of international application PCT/FR92/0544, filed Jun. 17, 1992.

Nucleic Acid Research, Vol 11, No. 3, February 1993, Arlington, Virginia, pages 555–573 describes native molecules of murine interferon α 1 and α 2. GB-A-2 157 697 describes native molecultes of bovine interferon α. WO-A-8 805 783 desribes peptides homologous to a fragment of the retroviral molecule of murine virus MLV p15E, these peptides being endowed with suppressive properties, also the use of these peptides as immunizing agents against a retroviral infection or on the contrary to induce an immunosuppression.

The present invention relates to immunogenic compounds with in particular an anti-cytokine effect, a preparation process, pharmaceutical compositions and kits containing them.

The present invention has two subjects:
1) Compounds which are all prepared and used as active immunization agents (vaccination). They are:
   compounds derived from a cytokine through loss of the biological activity characteristic of the cytokine, which are capable of inducing an immune response in vivo in contrast with native cytokine,
   peptide sites of HIV-1 selected because of their possible interference with the activation processes of T-cells,
   HIV virus particles depleted of their genomic RNA, as well as pharmaceutical compositions containing them.
2) A prophylactic or therapeutic treatment consisting of an anti-cytokine vaccination and aiming to repair homeostatic disorders caused by over-production of a cytokine. This new vaccination strategy could be used on its own or, in the case of a microbial infection, combined with a conventional vaccination (active immunization directed against the infectious agent).

Cytokines are proteins which modulate cell activity or proliferation, whose production is generally local and transitory and which act in a paracrine or autocrine manner. In what follows, the term "cytokine" incorporates families of endogenic molecules of various denominations: lymphokines, monokines, interleukins, interferons, colonization factors and growth factors, neuro peptides.

The known cytokines are in particular interferon-α (IFN-α), interferon-β (IFN-β), gamma-interferon (gamma-IFN), interleukin-1 (IL-1) in α and β forms, interleukin-2 (IL-2), interleukin-3 (IL-3), interleukin-4 (IL-4), interleukin-5 (IL-5), interleukin-6 (IL-6), interleukin-10 (IL-10), tumor necrosis factor (TNF) in α and β forms, transforming growth factors (TGF-β), in β1, β2, β3, β1.2 forms, and colony-stimulating factors (CSF) such as the granulocyte macrophage-stimulating factor (GM-CSF), the granulocyte colony-stimulating factor (G-CSF) and the macrophage-stimulating factor (M-CSF) and the epithelial growth factor (EGF), somatostatin, endorphins, the various "releasing factors" or "inhibitory factors" such as TRF.

Certain pathological states due to an infection, such as AIDS or herpes, can stem from homeostatic disorders induced by an over-production of cytokine(s) such as IFN-α or TNF.

Other pathological conditions (malignant tumor, allergy, auto-immune illness) can also be the consequence of homeostatic disorders.

In order to treat some of these pathological conditions, the use of anti-cytokine-neutralizing monoclonal antibodies (MAbs) was proposed for therapeutic purposes. Some of them have already been successfully experimented with. Such MAbs are intended to neutralize hyperproduction of a cytokine.

It is now proposed to substitute this passive therapy of serotherapy type with an active therapy of vaccinal type which consists of the administration of an inactivated immunogenic cytokine, or of one of its inactivated analogues. In fact it is a question of inducing an immune response of the organism against the native cytokine which is produced in excess. This active therapy, just like the administration of MAbs, would bring about a "buffer" effect, but it would certainly be in a more refined and more suitable manner. In addition, this new therapy avoids the necessity of humanizing the MAbs of animal origin (murine) which is a long and delicate stage in the development of MAbs for therapeutical purposes.

On the other hand, IFN-α, -β as well as TGF-β are in particular known as growth inhibitors of the immunity cells (cytostasis).

The immune system is presented with two functional aspects: non-specific immunity and specific immunity, also called memorized immunity. Non-specific immunity consists of a first line of defence, capable of stopping most of the pathogenic agents before a real infection is established. The mechanisms of specific immunity then come into action. They release a reaction directed specifically against the responsible germ, bringing about its destruction.

The phenomena of specific and non-specific immunity are the purpose of cells and molecules distributed throughout the organism. Non-specific immunity uses in particular phagocytic cells and killer or NK (natural killer) cells as well as soluble factors such as lysozyme, complement and a family of antiviral agents with a wide range of action, that is the interferons.

Subsequently, it was revealed that the interferons can be produced under physiological or physiopathological conditions which are not necessarily associated with viral infections. In fact a certain number of interferon synthesis inducers exist which are non-viral substances.

In addition to their anti-viral effect in the simple control of an infection, interferons possess an anti-proliferative (cytostatic) activity in vivo which gives them anti-tumor properties, and immunoregulatoty properties of specific immune reactions. However, everyone agrees that this regulatory effect is extremely complex.

Acquired specific immunity is itself the phenomenon of a co-operation of macrophages, B lymphocytes (humor-mediated immunity) and T lymphocytes (cell-mediated immunity).

In a general and schematic manner, there exist two major types of specific immune response: humoral-type response which is characterized by the production of antibodies by the B lymphocytes and cell-mediated immune response which uses effector cells, that is essentially the $T_8$ lymphocytes (cytotoxic lymphocytes). These responses are initially activated by antigen-presenting cells and modulated by regulatory cells, that is the $T_4$ lymphocytes (auxiliary T lymphocytes) and the suppressor T lymphocytes.

In its three major lines, the specific immune response functions as follows:
   Antigen-presenting cells (monocytes, macrophages and B lymphocytes) capture the antigen, digest it and re-expose fragments of it on their surface, in combination with molecules of the major histocompatibility complex (MHC) of class I or II.

When the $T_4$ lymphocytes "see" the antigen fragments combined with the major histocompatibility complex of class II, they proliferate, pass into activated form (synthesize IL-2), and in doing this stimulate the proliferation of the antibody-producing B lymphocytes and that of the $T_8$ lymphocytes (cytotoxic lymphocytes or CTL).

The B lymphocytes produce antibodies which interact with the circulating antigens so as to neutralize them.

Finally, the $T_8$ lymphocytes destroy the infected cells when they recognize the antibody fragments combined with the major histocompatibility complex of class I.

The standard immune response to any microbial agent can be schematically summarized as followed: the intervention of the non-specific immunity is almost immediate, then, if appropriate, it is followed within 48 to 72 hours by the appearance of the specific immune response. However, there are notable exceptions, in particular when the microbial agent is a virus. In this case, the absence of or the difficult induction of a specific immune response is sometimes observed.

The absence of induction could be explained by a suppressor effect induced by the viral agent due to an overproduction of cytokines such as IFN-α. These could prevent or halt the establishment of the immune response.

What precedes explains the failure of certain vaccination attempts. In fact, strongly immunogenic elements, which are potential candidates as vaccines (inactivated or attenuated virus or bacterium; proteins of viral, bacterial or parasitic origin) sometimes prove insufficient during tests in vivo, such as in AIDS or herpes.

HIV infections (human immunodeficiency virus) represent a typical case of what has just been mentioned. Quite particularly, the presence of IFN-α, and of neopterin and of $\beta_2$ microglobulin which are markers of IFN-α production was observed in a significant quantity in the blood of patients presenting an HIV infection (human immunodeficiency virus) whilst the blood of healthy individuals contains no detectable quantity of IFN-α; the presence of corpuscles associated with the secretion of IFN-α was also observed in the ganglia of individuals infected with HIV.

Furthermore, in a culture in vitro of PBLs (peripheral blood lymphocytes: lymphocytes+macrophages) originating from patients at the ARC or AIDS stage, the production of IL-2 is significantly improved when the PBLs have been treated with an anti-IFN-α serum.

An HIV infection is detected in its very initial stage by a seropositivity of the patient which persists subsequently. In a typical manner, this infection develops over the years from the asymptomatic stage to the fulminant stage of acquired immunodeficiency syndrome (AIDS) passing through a persistant and generalized lymphadenopathy (PGL) and a pre-AIDS stage or an AIDS-related complex (ARC) stage. Alongside this infection, associated clinical manifestations (or opportunistic infections) quite often develop such as *Pneumocystis carinii* pneumonias, cytomegalovirus infections, and tumors such as Kaposi's sarcoma. In short, an HIV infection neutralizes the defences of an individual by completely diverting its immune system.

The target of the HIV virus is the cells of the immune system expressing the $CD_4$ membrane marker, essentially the $T_4$ cells and the macrophages. During an infection, the number of circulating $T_4$ lymphocytes decreases progressively at the PGL and ARC stages and falls dramatically at the AIDS stage. Thus the selective loss of $T_4$ lymphocytes and macrophages resulting from the cytostatic activity of the HIV is the direct reflection of the phenomenon of immunodeficiency. This mechanism can recognize different etiologies, amongst which is the appearance of suppression factors.

It would also be desirable to have available anti-cytostatic derivatives permitting the activity of these suppression factors to be blocked.

It has now been found that in particular an IFN-α, in an immunogenic and inactivated form, or a fragment or inactive analogue, was capable of stimulating the immune response of an individual and therefore of inducing in the organism an anti-suppressive property against the immunity cells (property called anticytostatic).

This is why a subject of the present invention is an inactivated immunogenic cytokine or an inactive analogue or a cytokine fragment.

By "immunogenic cytokine" is meant a cytokine capable of inducing an immune response even in the species from which it originates, knowing that the corresponding native cytokine (cytokine substantially as found in a species) is incapable or only very slightly capable of it. For example, a cytokine of human origin administered in immunogenic form (a form which is different from the native form) to a human, induces an anti-cytokine response which is usually manifested at least by the production of antibodies which recognize both the administered cytokine and the native cytokine. Among these antibodies, the neutralizing antibodies are in particular capable of inhibiting the biological activity of native cytokine. More particularly, it is considered that an immunogenic cytokine is capable of inducing a humoral or cellular immune response in most individuals of the same species.

By "inactivated cytokine or an inactive analogue" is meant a cytokine or cytokine fragment which has lost or has no biological activity; that is to say which is not capable of acting as a regulator of the activity of cell proliferation.

By "inactive cytokine" is meant an analogue of a cytokine as found in another species, which has no biological activity in the species to which it is administered and whose amino acid sequence differs from the natural sequence by at least one amino acid residue; the degree of homology is not however less than 50% and preferably not less than 80%.

By "inactivated cytokine" is meant a cytokine or inactive cytokine which has lost its biological activity and which was obtained from a native cytokine (the native cytokines which are available are usually produced by genetic engineering techniques and have in particular undergone a chemical, physical or immunological treatment or also after encapsulation in an emulsion in proteosomes or liposomes in order to inactivate them).

By "inactive cytokine fragment" is meant a fragment of a cytokine as found in a species, which has no biological activity in the species to which it is administered, notably in man and the amino acid sequence of which differs from the natural sequence by at least one amino acid residue; the degree of homology is not however less than 50% and preferably not less than 80%. Such a fragment can have 4 to 100 amino acids for example and preferably 6 to 60 amino acids and in particular 6 to 20. It can be made by peptide synthesis or by genetic engineering (notably bacteria or recombinant eukaryote cells).

Advantageously, a cytokine according to the invention is of murine origin or preferably of human origin.

By "inactivated cytokine of human origin" is meant an inactivated cytokine obtained from a human cytokine.

Preferably, a cytokine according to the invention is an immunogenic and inactivated cytokine.

A cytokine according to the invention is preferably selected from an IFN-α, an IFN-β, an IFN-gamma, an interleukin (IL), notably an IL-2, an IL-4, an IL-5, an IL-6, a TNF α or β and a TGF-β and notably an interferon-gamma, an interleukin-1, an interleukin-2, an interleukin-4, an interleukin-5, an interleukin-6, an interleukin-10 (IL-10) and a transforming growth factor-β or an inactive or inactivated fragment of said cytokines. There are more particularly preferred a TGF-β, an IFN-β and an IFN-α according to the invention; the latter is quite particularly preferred.

Also a subject of the invention is a preparation process for an immunogenic and inactivated cytokine or for an inactive fragment of cytokine, which comprises the action of inactivating a cytokine and making it immunogenic by subjecting it to an immunological, physical or chemical treatment. It should be noted that one and the same treatment can cause it to lose its biological activity and make it immunogenic.

An appropriate physical treatment can be a treatment with heat or radiation exposure, an encapsulation (water-in-oil emulsion or inclusion in vesicles such as liposomes and proteosomes). A suitable chemical treatment can be a treatment with an aldehyde such as formaldehyde or a polyaldehyde or other compounds (β-propiolactone or polyethyleneglycol for example). A treatment with formaldehyde is particularly preferred.

In a typical manner, 100 μg to 10 mg of cytokine/ml is treated with formaldehyde having a final concentration of 10 mM to 100 mM, at a temperature of 10 to 60° C., for 2 to 15 days. This data is supplied only as an example. Of course each of the parameters varies as a function of the others; for example when the concentration of formaldehyde increases, the duration of the reaction can be reduced without prejudice.

Also a subject of the invention is cytokines or cytokine fragments in inactivated and immunogenic form obtained by implementing the processes described above, preferably of human origin, notably those described above.

As has been seen, the cytokines, fragments or analogues according to the invention present remarkable properties: they are in particular capable of inducing an immune response in the individual to whom they are administered (reaction of humoral and cellular type) in the form of a vaccine, but acting in the case of a hyperproduction of cytokines disrupting homeostasis to correct these disruptions. The products according to the invention have the advantage of only making their effects felt during these disruptions.

They do not cause significant clinical or biological side effects.

During the evolution of HIV infection, the individuals abnormally produce IFN-α, contributing to a cytostatic effect on the immunity cells. Miniscule doses of IFN-α in fact block the proliferation of normal cells (such as blood TLs of normal individuals); furthermore anti IFN-α antibodies partially restored the proliferation and the production of IL-2 by TLS of patients suffering from AIDS.

Also, the over-production of other cytokines contributes to the appearance of other pathological conditions:

This is the case in particular for IL-4 which is a cofactor for stimulation of B-lymphocytes (BL) inducing the production of IgE by said BLs. These IgEs, by their power of degranulation of the basophiles and mastocytes, contribute to pathological manifestations linked to allergy.

This is the case also for example for IL-6 which contributes to the secretion of Ig (immunoglobulins) by the cancerous cells of myeloma.

The administration of cytokines, fragments or analogues according to the invention produces an immune reaction of the organism which restores the compromised balance due to the humoral and cellular immune response (antibodies or anti-cytokine killer cells concerned).

The cytokines, fragments or analogues according to the invention can therefore be used according to the cytokine concerned both as a curative and a preventative notably in the treatment of AIDS for IFN-α, in the treatment of allergy for IL-4 and IL-5, in the treatment of certain auto-immune illnesses (lupus erythematosus, rhumatoid polyarthritis, dermatosclerosis . . . ), the treatment of certain cancerous illnesses such as multiple melanoma for IL-6, and more generally the other illnesses brought about by the disruption of an excess of cytokines (including as has been seen the neuropeptides such as somatostatin).

The derivatives according to the invention have a very weak toxicity both for animals and man. Doses of 20 mg administered to a mouse on days 0, +21, +41 did not produce any toxicity. A dose of 200 to 400 mg injected in man by intramuscular route of the derivative of Example 1 for example did not produce any detectable toxic effect.

These properties justify the use of cytokines, fragments or analogues according to the invention as medicaments.

This is why a subject of the present invention is also:
a) A pharmaceutical composition containing as therapeutic agent a cytokine or fragment or analogue of cytokine according to the invention.
b) A pharmaceutical composition intended for the treatment of a malignant tumor such as a multiple myeloma whose secretion of Ig is linked to IL-6, of an auto-immune illness or of an allergy (urticaria, allergic rhinitis) associated with the hyperproduction of Ig, linked to the over-production of IL-4 or IL-5 which contains, as therapeutic agent, a cytokine, fragment or analogue according to the invention selected from an IL-6, a TGF-β, an IL-1, an IL-2, an IFN-gamma, an IL-5 and an IL-4.
c) A pharmaceutical composition intended for the stimulation of the immune defences of an individual, which contains, as therapeutic agent, a cytokine, fragment or analogue according to the invention selected from a TGF-α, an IFN-β, a TNF and an IFN-α according to the invention.
d) A pharmaceutical composition intended for the treatment of an HIV infection, preferably HIV-1, which contains as therapeutic agent an IFN-α, fragment or analogue of IFN-α according to the invention.

These pharmaceutical compositions usually contain an acceptable pharmaceutical excipient as well as a therapeutically effective quantity of active ingredient.

A pharmaceutical composition as listed in d) is of quite particular interest when treating an HIV infection in a therapeutic prophylactic manner in the ARC or AIDS stage or associated clinical manifestations. In fact, an IFN-α according to the invention has an anti-cytostatic activity against the $T_4$ lymphocytes of patients and therefore promotes the maintenance, if not the growth, of the number of $T_4$ lymphocytes, with the direct consequence of maintaining or increasing the activity of the cytotoxic T lymphocytes. This can be shown in a CMI test (cell-mediated immunity) as described in Example 4 hereafter.

A pharmaceutical composition listed in c) or d) can in addition contain a conventional vaccinal agent. By "conventional vaccinal agent" is meant:
(i) A pathogenic agent treated or modified to make it non-infectious; this can be for example a complete bacterium or a virus which has lost its infectious character due to a chemical treatment (inactivated vaccinal agent) or whose virulence has been reduced by mutagenesis or by passage through a medium which causes mutations (killed vaccinal agent);

(ii) An antigenic determinant characteristic of a pathogenic agent, in a form isolated from said pathogenic agent (sub-unit vaccinal agent); this can be for example a bacterial toxin or a fragment of the latter, a specific antigen of an infectious agent such as a capsular polyoside or a fragment of the latter, a viral protein for example an envelope or capsid viral protein or a fragment of the latter and a parasitic antigen or a fragment of the latter, this list being however non-limitative; or (iii) An antigenic determinant characteristic of a tumor.

In addition, the invention also proposes a kit containing:

a) A pharmaceutical composition intended for the stimulation of the immune defences of an individual, which contains as therapeutic agent a cytokine, fragment or analogue according to the invention selected from a TGF-β, an IFN-β and an IFN-α according to the invention or also a TNF;

b) A conventional vaccinal pharmaceutical composition, and c) Instructions for the concomitant or consecutive administration of compositions a) and b).

By "conventional vaccinal composition" is meant a composition which contains a conventional vaccinal agent, that is to say at least one specific antigen of the pathogenic agent against which the vaccination is directed.

A pharmaceutical composition according to the invention can in addition contain an adjuvant. Generally, the presence of an adjuvant permits the dose of the therapeutic agent relative to a composition which would not contain any therapeutic agent to be reduced.

Finally, a pharmaceutical composition according to the invention can be produced in a conventional galenic form. In particular a cytokine according to the invention is combined in a sufficient quantity to be therapeutically effective with a pharmaceutically-acceptable diluting agent or support. A composition according to the invention can be administered by any conventional route used in the domain of vaccines, in particular by sub-cutaneous route, by intramuscular route or by intravenous route, for example in the form of an injectable suspension.

The administration can take place as a single dose or as a dose repeated one or more times after a certain interval. The suitable dose varies as a function of various parameters, for example, the individual treated or the administration method. By way of example, it can be indicated however that inpatients having an HIV infection, satisfactory results are obtained with a dose of IFN-α according to the invention of 1 to 50 μg/kg of mammal, advantageously of 3 to 20 μg/kg of mammal, preferably 3 to 8 μg/kg of mammal. The lowest doses are advantageously administered in the presence of adjuvants and/or at repeated intervals whilst the highest doses can be administered in one lot and/or in the absence of an adjuvant.

Also, a subject of the invention is:

e) The use of a cytokine fragment or analogue according to the invention for therapeutical purposes; in particular, the use of an IL-6, a TGF-β, an IL-1, an IL-2, an IFN-gamma, an IL-4 or an IL-5 according to the invention for the treatment of a tumor, an auto-immune infection or an allergy; quite particularly, the use of a TGF-β, an IFN-β or an IFN-α according to the invention for stimulating the immune defences of an individual for example for enhancing the vaccinal power of a conventional vaccinal agent; preferably, the use of an IFN-α according to the invention for treating a viral infection by an envelope virus, notably HIV.

f) A therapeutic treatment method which comprises the action of administering a cytokine, fragment or analogue according to the invention in a sufficient quantity to be therapeutically effective to a patient who needs such a treatment.

g) The use of a cytokine, fragment or analogue according to the invention for preparing a pharmaceutical composition intended for the treatment of a malignant tumor and/or of an auto-immune illness and/or of an allergy and/or for the stimulation of the immune defences and/or treatment of an infection by an envelope virus, particularly HIV, notably obtained by the preparation process defined above.

It has also been found that in the case of an infection with an envelope virus, notably a retrovirus, the immuno-suppressive effect could not only be attributed to a hyper-production of cytokines such as IFN-α in the case of infection with HIV-1 by the infected cells but also to the blocking of the activation of TLs (anergy phenomenon) by peptide elements of the retrovirus itself. These elements act either directly, or by homology with the site of an immuno-regulatory substance (mimicry or inhibition) this is the case for the peptide identified by the sequence identifier (hereafter SI) No. 6 below.

More particularly, certain sites responsible for this inhibiting activity were located in particular on the sub-units of env proteins, (gp 120 and gp 41) and gag of envelope viruses.

Consequently, the invention proposes a peptide having a cytostatic activity against cells of the immune system containing an amino acid sequence substantially identical to the sequence of a region of one of the sub-units of the gag or env protein of an envelope virus; said sequence of a region of one of the sub-units of the above protein containing or being adjacent to a peptide having at least 50%, advantageously at least 70%, preferably at least 80% and most preferably at least 90% homology with the sequence of an active segment of a human protein having an immuno- regulatory, in particular cytostatic, activity.

By "active segment" is meant the site carrying the activity, or said site as well as the sites which are adjacent to it, or also the adjacent sites insofar as the antibodies directed against these adjacent sites functionally block the site carrying the activity.

By "sequence substantially identical to another sequence" is meant a sequence which has a degree of homology of at least 50%, advantageously of at least 90%, preferably of at least 95% with the other sequence.

The peptides according to the invention are presented in immunogenic form, and denuded of immuno-suppressive activity.

A preferred peptide according to the invention contains:

(i) An amino acid sequence substantially identical to the sequence of a region of one of the sub-units of the gag protein or the env protein of a retrovirus, notably the HIV-2 and HIV-1 viruses, particularly the latter, this sequence itself containing a peptide having a homology preferably of at least 50%; or (ii) an amino acid sequence substantially identical to the sequence of a region of one of the sub-units of the gag protein or the env protein of an HIV virus.

A peptide according to the invention advantageously contains at least 5 amino acids and at most 50 amino acids, preferably at most 30 amino acids.

There is in particular preferred a peptide according to the invention which contains an amino acid sequence substantially as shown in the sequence identifier (SI) No. 1a, 2a, 3a or 4 (corresponding to SEQ ID NOs:1, 2, 5 and 7, respectively). Those shown in the SI Nos 7, 8, 11, 12 (corresponding to SEQ ID NOs:10, 11, 14 and 15, respectively and notably 5, 6, 7 and 10 (corresponding to SEQ ID NOs:8, 9, 10 and 13, respectively are also preferred.

The peptides can be used directly in water-in-oil emulsions or set in aqueous adjuvants of calcium phosphate or also adsorbed in an aluminium phosphate. The peptides can also be presented conjugated with carrier proteins, such as tetanus toxoid or also KLH. Finally, the peptides can also be presented in bacteria in genetic recombination constructions, after the insertion of suitable nucleotide sequences in the plasmids.

Certain non-immunogenic and immuno-suppressive peptides are new, notably those shown in SI 6 to 12, (corresponding to SEQ ID NOs:9–15), in particular SI 6 and 7 (corresponding to SEQ ID NOs: 9 and 10). These peptides are also a subject of the invention.

A pharmaceutical composition according to the invention is advantageously intended for the prevention or treatment of an HIV infection, more particularly intended for the treatment of an HIV infection at the ARC or AIDS stage.

The immunogenicity of a peptide according to the invention can be given by the preparation of proteosomes or by the use of a pharmaceutically-acceptable lipid compound which preferably has the properties of an adjuvant.

For example, a composition according to the invention can be prepared by diluting a peptide according to the invention in a water/oil suspension. On the other hand, suitable proteosomes are as described and obtained in Lowell et al, J. Exp. Med., (1988) 167: 658. When a peptide according to the invention is combined with proteosomes, it is preferably prepared in the form of a conjugate, that is to say that it is linked by covalent bonding to a hydrophobic group such as a fatty acid radical, for example a lauryl or lauryl-Cys radical, or it contains in addition to the characterizing sequence, a base-sequence composed of hydrophobic amino acids, for example, Phe-Leu-Leu-Ala-Val-Phe-Cys; (corresponding to amino acid residues 1–7 of SEQ ID NO:2) the base-sequence is preferably linked by peptide bonding to the $NH_2$-terminal end of the characterizing sequence.

The above products are endowed with remarkable properties which justify their use as medicaments.

Native peptides (isolated or obtained by synthesis or genetic engineering) can be used to induce an immunosuppression; such a property is illustrated below in the experimental part for the SI Nos 5, 6, 7 and 10 (corresponding to SEQ ID NOs:8, 9, 10 and 13, respectively).

Inactivated and made immunogenic, they can be used to induce, in the organism considered, a cellular and humoral immune response neutralizing the biological effects of these peptides.

Peptides in inactivated but immunogenic form could be used as above.

This is why a subject of the present Application is also medicaments characterized in that they are constituted by the native or modified peptides defined above, as well as the pharmaceutical compositions containing them. The above medicaments can be used, as far as the immunogenic peptides are concerned, as a treatment for creating an active immunization against pathogenic agents containing them: for example against the glycoproteins gp 160, 120 or 41 of HIV-1 which contain for example the Ile-Leu-Ala Val-Glu-Arg-Tyr (corresponding to amino acid residues 19–25 SEQ ID NO:8) site homologous with the active site of IFN-α, or the Leu-Glu-Arg-Ile-Leu-Leu (SEQ ID NO:16) site corresponding to the bonding site of IL-2 with its receptor (IL-2R).

Also:

The Ser-Leu-Trp-Asp-Gln (amino acid residues 6–10 of SEQ ID NO:9) peptide is completely identical between the HIV-1 envelope (residues 110 to 114) and the CD4 (residues 60 to 64). See SI No. 6

The Cys-Thr-Ala-Ser-Gln-Lys (SEQ ID NO:17) peptide of the CD4 molecule (residues 16–21) shares a strong homology with the envelope of HIV-1 (Cys-Ser-Ala-Thr-Glu-Lys, residues 28 to 33 and corresponding to amino acid residues 1–6 of SEQ ID NO:10). See SI No. 7 The Glu-Pro-Thr-Ala-Pro-Pro (amino acid residues 8–13 of SEQ ID NO:11) peptide is common between the CD5 and the gag protein of HIV-1, and unique to these two molecules amongst all the known proteins. It corresponds to residues 454–459 of HIV-1 gag and to residues 153–158 of the CD5 receptor. See SI No. 8

The Thr-Thr-Leu-Phe-Cys-Ala (SEQ ID NO:18) peptide (residues 20 to 25) of the HIV-1 envelope has a very strong homology with the Thr-Thr-Leu-Phe-Cys-Leu (amino acids 4–9 of SEQ ID NO:12) peptide of the TNF alpha (residues 45 to 50). See SI No. 9

The Leu-Leu-Leu-Asn-Gly-Ser-Leu-Ala (amino acid residues 2–9 of SEQ ID NO:13) peptide of the HIV-1 envelope (residues 259–267) has a significant similarity to the following regulatory molecules: HLA of class I (residues 11–18), β chain of the T-cell receptor (residues 14 to 21), and G-CSF (residues 17 to 24). See SI No. 10.

The Gln-Leu-Thr-Val-Trp (amino acid residues 5–9 of SEQ ID NO:14) peptide is common to the HIV-1 envelope (residues 566–570) and to the chain of the T-cell receptor (residues 130–134). See SI No. 11.

The Gly-Ile-Arg-Pro-Val-Val (amino acid residues 2–7 of SEQ ID NO:15) peptide of the HIV-1 envelope (residues 250–256) has a very strong homology with the Gly-Ile-Arg-Val-Val (SEQ ID NO:19) peptide of the α chain of the precursor of the leukocyte adhesion protein (residues 230–236). See SI No. 12.

Similarly, an immunization can also be created against peptides originating from active sites of other envelope viruses inducing an immunosuppression, notably those of the herpes family, HIV-2, HTLV1 and the flu virus.

With regard to the non-inactivated, immunosuppressive active peptides, they can be used in particular in the treatment of transplant rejections.

They can be administered as a curative or preventative treatment.

The immunogenic peptides have a very weak toxicity; administered at a dose of 20 μg to a mouse, no toxicity was observed.

A pharmaceutical composition according to the invention can in addition contain a conventional anti-infectious agent, intended for vaccination against a retrovirus infection, notably HIV. For use against an HIV infection, an advantageous conventional vaccinal agent is for example the env protein in the form of the non-cleavable gp160 protein, the sub-unit gp 120 of the env protein, a fragment of the gp120 containing the $V_3$ loop or HIV virions depleted of their genomic RNA.

Finally, a pharmaceutical vaccinal composition according to the invention can be produced in a conventional manner. In particular, a peptide according to the invention is combined in a sufficient quantity to be therapeutically effective with a pharmaceutically-acceptable solvent or support. A composition according to the invention can be administered by any conventional route used in the domain of vaccines, in particular by sub-cutaneous route, by intra- muscular route, by intravenous route or by intradermal route, for example in the form of an injectable suspension, or also by oral route. The administration can take place as a single dose or as a dose repeated one or more times after a certain interval. The dose varies as a function of various parameters, for example, of the individual treated or of the administration method. By way of example, it is indicated however that, in patients having an HIV infection, satisfactory results are obtained with a dose of each of the peptides of SI Nos 1a, 2a, 3a, 4, 5, 6 and 7 (corresponding to SEQ ID NOs:1, 3, 5, 7, 8, 9 and 10respectively) at 20 μg/kg of body weight, advantageously 4 to 16 μg/kg of body weight, preferably 8 to 12 μg/kg of body weight, both presented in the form of proteosomes and coupled with toxoids or emulsified.

The lowest doses are advantageously administered in the presence of adjuvants and/or at repeated intervals whilst the highest doses can be administered in one lot and/or in the absence of an adjuvant.

Also an alternative invention proposes:
(i) A kit containing:
  a) A pharmaceutical composition according to the alternative invention,
  b) A conventional pharmaceutical vaccinal composition, and
  c) Instructions for the concomitant or consecutive administration of compositions a) and b).
ii) The use of a peptide according to the invention for preventing or treating an envelope virus infection, particularly a retrovirus, notably HIV.
iii) A method for preventing or treating an envelope virus infection, particularly a retrovirus, notably HIV, which comprises the action of administering a peptide according to the invention in a sufficient quantity to be therapeutically effective and in combination with an element capable of inhibiting the potentially cytostatic activity of said peptide, to a patient who has a need for such a treatment.
(iv) The use of a peptide according to the invention for preparing a pharmaceutical composition intended for the prevention or the treatment of an envelope virus infection, particularly a retrovirus, notably HIV, notably at the ARC or AIDS stage and notably by the production process defined above.

The invention also relates to a virus depleted of its genome, namely which no longer contains any genomic nucleic acid of said virus. RNA viruses depleted of said RNA are preferred, notably those with an envelope.

A virus depleted of its genome according to the invention is advantageously derived from an envelope virus, notably a retrovirus, preferably an HIV virus. Also the invention proposes a preparation process for a virus depleted of its genome, which comprises:
a) the action of subjecting a virus to an alkaline hydrolysis (for an RNA virus) or an acid hydrolysis (for a DNA virus), and
b) the action of collecting a virus depleted of its genome obtained in a).

In a more particular aspect, a process according to the invention can be notably implemented according to the following alternative.

The first comprises:
a) the action of subjecting a virus to an alkaline hydrolysis,
b) the action of treating a virus depleted of its genome obtained in a) with an aldehyde and,
c) the action of collecting the virus depleted of its genome obtained in b).

The second comprises:
a) the action of treating a virus with an aldehyde,
b) the action of subjecting the virus obtained in a) to an alkaline hydrolysis, and
c) the action of collecting a virus depleted of its genome obtained in b).

The same goes for the acid hydrolysis. An advantageous aldehyde is formaldehyde or a polyaldehyde such as glutaraldehyde; these last two being preferred. The alkaline hydrolysis intended to depolymerize the RNA can be notably used in the presence of any compound which hydrolyzes RNA; for example sodium hydroxide or potassium hydroxide, the latter being preferred. The same goes for the acid hydrolysis. As acids there can be mentioned in particular acetic acid. The depleted viruses according to the invention are endowed with remarkable properties. They are in particular immunogenic, inducing a humoral or cellular immune response; such a property is illustrated below in the experimental part. Also, they have lost their infectious power. These properties justify their use as a preventative or curative medicament.

The depleted viruses according to the invention show no detectable toxicity in man or animals.

They can be used in particular in the treatment of viral illnesses: notably of HIV-1, HIV-2, HTLV-1, FELV, FIV and the other infections caused by an envelope virus, notably those of the herpes family.

A composition according to the invention intended for the prevention of a retrovirus infection is a vaccinal composition in which a virus depleted of its genome according to the invention is present as an immunogen.

A pharmaceutical composition according to the invention can in addition contain an adjuvant. Generally, the presence of an adjuvant permits the dose of the therapeutic agent relative to a composition which would not contain any therapeutic agent to be reduced.

Finally, a pharmaceutical composition according to the invention can be produced in the conventional manner. In particular, a peptide according to the invention, in sufficient quantity to be therapeutically effective, is combined with a pharmaceutically-acceptable solvent or support.

A composition according to the invention can be administered by any conventional route in use in the domain of vaccines, in particular by sub-cutaneous route, by intramuscular route or by intravenous route, for example in the form of an injectable suspension. It can also be administered by oral route. The administration can take place in a single dose or in a dose repeated one or more times after a certain interval. The suitable dose varies as a function of various parameters, for example the individual treated or the administration method. By way of example, it should be indicated however that in patients having an HIV infection, satisfactory results are obtained for example with a dose of HIV virus depleted of its genome of 10 to 40 μg/kg of body weight, advantageously 20 to 30 μg/kg of body weight. The lowest doses are advantageously administered in the presence of adjuvants and/or at repeated intervals whilst the highest doses can be administered in one lot and/or in the absence of an adjuvant.

The invention is illustrated below:

EXAMPLE 1:

Inactivation of an IFN-α in the presence of formaldehyde.

Sodium phosphate (70 mM final concentration) and formaldehyde (33 mM final concentration) are added to 8 ml of a solution of IFN-α with 1 mg of protein/ml (Hoffmann-Laroche). Incubation is carried out for 3 days at 37° C. without agitation. Lysine 1 mg/ml (final concentration) is added.

The preparation is then dialyzed against a PBS pH 7.2 buffer diluted 10 times (phosphate buffer saline; 20 mM of sodium phosphate and 150 mM of sodium chloride) for 3–4 hours at 4° C. Then the dialyzate is divided into 20 doses of identical volume and each of the doses is lyophilized.

EXAMPLE 2

Formulation of peptides into proteosomes.

The peptides having a sequence as shown in the SI Nos. 1b to 3b and 5 were synthesized by Neosystem (Strasbourg, France) and prepared separately in the form of lyophilizates. Each of the lyophilizates is taken up in a TE buffer (50 mM Tris pH 7.4; 0.5 mM EDTA) with 1% Empigen BB detergent (Albright & Wilson, Whithaven, Cumbria) in order to obtain a 2 mg/ml solution of the peptide.

Equal quantities of each of the peptide solutions are mixed together which subsequently have a solution of proteosomes prepared according to the method of Lowell et al. J. Exp. Med. (1988) 17: 658, added to them in a ratio of peptides:proteosomes of 8:1 (weight/weight).

This preparation is dialyzed against PBS at 4° C. for 10 days under sterile conditions. After dialysis, the preparation contains approximately 200 ug/ml of proteosomes and approximately 800 μg/ml of peptides fixed in the proteosomes.

EXAMPLE 3

Preparation of a pharmaceutical composition based on inactivated IFN-α and peptides.

3A) Composition No. 1

400 μl of a 35 mM calcium phosphate and 35 mM sodium chloride solution pH 7.2 is centrifuged. The supernatant is eliminated. The pellet of calcium phosphate is taken up in 400 μl of the preparation as obtained in Example 2.

Finally, this 400 ul is used to dissolve a dose as obtained in Example 1 (containing 400 μg±200 μg of inactivated IFN-α).

3B) Composition No. 2

A dose as obtained in Example 1 and 500 μg of the lyophilizate of each of the peptides having a sequence as shown in SI Nos. 1b to 3b and 5 are mixed together and taken up in a water/mineral oil suspension ref. ISA 724 (Seppic, France).

EXAMPLE 4

Treatment of patients having an HIV infection at ARC stage with inactivated IFN-α and/or peptides.

Four patients K11, K41, K80 and K711 having an HIV infection at ARC stage were medically monitored from November–December 1986 (K11, K41 and K80) or from January 1989 (K711). In particular they were subjected to an immunotherapy which consists of injections repeated at intervals varying from 1 to 8 months, of autologous PBL (peripheral blood lymphocytes=lymphocytes+macrophages) infected in culture in vitro by the HIV-1 virus. The last injection of autologous cells took place in May 1990.

From October 1990 the patients were subjected to a new immunotherapy, the protocol of which is indicated in the table below.

|  | K11 | K41 | K80 | K711 |
|---|---|---|---|---|
| OCTOBER 90 | P | P | P + I | P + I |
| FEBRUARY 91 | P | P + I | P + I | P + I |
| APRIL 91 | P | P + I | P + I | P + I |

The improvement of the immunity of each of the patients is monitored by measuring the quantity of $T_4$ lymphocytes (T-auxiliaries) per $mm^3$ of blood (it should be noted that in a healthy individual, the normal concentration of $T_4$ lymphocytes is of the order of 500 to 1,000 lymphocytes per $mm^3$ of blood) as well as by evaluation of the cell-mediated immune response in vivo and in vitro.

The evaluation in vivo is carried out using an intradermal test with candidin or tuberculin (Pasteur-Mérieux).

The evaluation in vitro is carried out using the CMI test; the latter being implemented as follows:

The blood sample is diluted to ⅓ in RPMI 1640 medium. The mononucleated cells are isolated by Ficoll-Hypaque gradient centrifugation for 25 minutes at 1,800 revs/min. The gradient interface is recovered and washed twice with RPMI 1640 medium (centrifugation at 1,500 revs/min. for 10 minutes). The total elimination of red corpuscles is checked by a cell count with 1% acetic acid and the viability of the mononucleated cells is ascertained with a trypan blue count.

The mononucleated cells are taken up in RPMI 1640 medium complemented with 10% human serum.

Aliquots of this preparation are distributed in round-bottomed wells of a micro-culture plate at the rate of $2\times10^5$ cells/well. An optimum quantity of antigen to be tested is added, that is to say candidin or tuberculin (optimum quantity to be determined according to the batches). The whole is in a volume of 200 μl/well.

The cell culture is continued at 37° C. in a humid atmosphere containing 5% $CO_2$ for 6 days. 18 hours before the end of incubation, 0.5 μCi of tritiated thymidine with a specific activity of 2 μCi/mole is added.

The cells are then collected on a filter, washed and dried. Finally the β radioactivity is measured.

The intensity of the immune response is proportional to the proliferation index $I_p$.

$$I_p = \frac{\text{radioactivity measured for the given antigen}}{\text{radioactivity measured for negative control}}$$

|  | K11 | K41 | K280 | K711 |
|---|---|---|---|---|
| 1. $T_4$ lymphocyte/$mm^3$ May 90 | 240 | 273 | 187 | 476 |
|  | 29% | 13% | 11% | 31% |
| 2. % $T_4$ lymphocytes April 91 | 247 | 440 | 348 | 1000 |
| (relative to all mononucleated cells) | 22% | 14% | 13% | 40% |
| Intradermal reaction May 90 test | – | – | – | – |
|  | – | – | – | – |

-continued

|  |  | K11 | K41 | K280 | K711 |
|---|---|---|---|---|---|
| 1. candidin |  | – | ++ | + | ++ |
| 2. tuberculin | April 91 | + | ++ | + | +++ |
| CMI test | May 90 | ND | ND | ND | ND |
| 1. candidin |  | ++ | + | + | ++++ |
| 2. tuberculin | April 91 | +++ | + | + | ++++ |

These results show an appreciable increase in the population of $T_4$ lymphocytes between May 90 and April 91 as well as a notable improvement in the capacity of the immune system of patients to reacting against an antigen.

EXAMPLE 5

Production of a suspension of viruses depleted of their HIV-1 genome starting with HIV-1 virions.
5A) Preparation No. 1

The supernatant of a culture of the H9/IIIB or MN $T_4$ lymphocyte line infected with the HIV1 virus, HTLV IIIB strain, is removed then centrifuged at 40,000×g at 4° C. for 2 hours. The pellet is resuspended in 1 to 2 ml of PBS pH 7.2 buffer. The suspension is centrifuged under the same conditions as previously. The pellet is again taken up in 100 ml of PBS. The total protein concentration of the suspension thus obtained is of the order of 2 mg/ml as determined by the Lowry method. The virion concentration of the suspension is estimated to have to correspond to about 50% of the total protein concentration. This estimation is based on an analysis by Western blot.

0.3N potassium hydroxide (final concentration) is added to 10 ml of the suspension obtained. The mixture is incubated overnight at 37° C. without agitation, then the preparation is neutralized with hydrochloric acid.

Then 70 mM (final concentration) of sodium phosphate pH 7.2 and 33 mM (final concentration) of formaldehyde is added to this preparation. At this stage, the preparation contains about 1 mg/ml of total proteins. This preparation is incubated for 3 days at 37° C. without agitation.

Then 0.5 mM (final concentration) of glutaraldehyde is added and the preparation is left to incubate for 30 minutes at ambient temperature. Finally, 1 mg/ml (final concentration) of lysine is added. The mixture is dialyzed against PBS diluted ten times, for 3–4 hours at 4° C. The dialyzate is then completely lyophilized.

5B) Preparation 2

10 ml of a preparation of HIV-1 virus in PBS buffer the protein concentration of which is of the order of 1 mg/ml is treated with formaldehyde according to the method set out in Example 5A. After the addition of lysine, treatment with potassium hydroxide is proceeded with as described in Example 5A. After neutralization, the preparation is dialyzed against PBS diluted 10 times for 3–4 hours at 4° C. Finally, the dialyzate is completely lyophilized.

EXAMPLE 6

Pharmaceutical composition based on the virus depleted of its HIV-1 genomes

6A) Composition No. 1

The lyophilizate obtained in Example 5A or 5B is taken up in 400 $\mu$l of apyrogenic sterile distilled water then mixed with 600 $\mu$l of an ISA 724 water/oil mixture.

6B) Composition NO. 2

The lyophilizate obtained in Example 5A or 5B, a dose of IFN-$\alpha$ as obtained in Example 1 as well as 500 $\mu$g of lyophilizate of each of the peptides having a sequence shown in SI Nos. 1B to 3B and 5 are taken up in 400 $\mu$l of apyrogenic sterile distilled water, then mixed with 600 $\mu$l of an ISA 724 water/oil mixture.

EXAMPLE 7

Treatment of patients having an HIV infection at ARC stage in particular with a virus depleted of its HIV-1 genomes.

Two patients K280 and G210 having an HIV infection at ARC stage were medically monitored from July 1986 and January 1990 respectively. In particular they were subjected to an immunotherapy which consists of injections repeated at intervals varying from 1 to 8 months of autologous PBL infected in culture in vitro by the HIV-1 virus. The last injection of autologous cells took place in May 1990.

From October 1990 the patients were subjected to a new immunotherapy the protocol of which is indicated in the table below.

| | K280 | G210 |
|---|---|---|
| OCTOBER 90 | S | S |
| FEBRUARY 91 | S + P + I | S + P + I |
| APRIL | S + P + I | S + P + I |

"P" represents a dose of 500 $\mu$g of each of the peptides having a sequence as shown in SI Nos. 1b to 3b and 5.
"I" represents a dose of 400 $\mu$g ± 200 $\mu$g of IFN-.
"S" represents a dose of the composition of the virus depleted of its genome as obtained in Example 6A corresponding to about 2 mg of protein.
"S + P + I" are injected in the form of a composition as obtained in Example 6B.

The improvement in the immunity of each of the patients is monitored by measuring the quantity of $T_4$ lymphocytes ((T-auxiliaries) per $mm^3$ of blood (it should be noted that in a healthy individual the normal concentration of $T_4$-lymphocytes is of the order of 500 to 1,000 $T_4$ lymphocytes per $mm^3$ of blood) as well as by evaluation of the cell-mediated immune response in vivo and in vitro.

The evaluation in vivo is carried out using an intradermal test with candidin or tuberculin (Pasteur-Mérieux).

The evaluation in vitro is carried out using the CMI test; the latter being implemented as described in Example 4.

The set of results is shown in the table below.

| | | K280 | G210 |
|---|---|---|---|
| 1. $T_4$ lymphocyte/$mm^3$ | May 90 | 396<br>22% | 780<br>29% |
| 2. % $T_4$ lymphocytes (relative to all mononucleated-cells) | April 91 | 448<br>21% | 1297<br>37% |
| Intradermal reaction test | May 90 | +<br>– | –<br>– |
| 1. candidin | | ++ | – |
| 2. tuberculin | April 91 | + | ++ |
| CMI test | May 90 | ND | ND |
| 1. candidin | | + | + |
| 2. tuberculin | April 91 | + | + |

These results show an appreciable increase in the population of $T_4$ lymphocytes between May 90 and April 91 as well as a notable improvement in the capacity of the immune system of patients to react against an antigen.

EXAMPLE 8

Proof of the immunosuppressive activity of the peptides.

T-cells originating from fresh human blood were placed in the presence of macrophages having an antigen (SEB, candidin etc . . . ) and in the presence or in the absence of peptides at a concentration of 100 to 500 µg/ml.

The cells are resuspended in the standard culture medium for lymphocytes.

After four days the activation of the cells is measured by the incorporation of labelled thymidine.

While the cells stimulated without peptides have a high activation level, the cells incubated with a peptide according to the invention have a low activation according to a dose-effect curve for the peptides SI Nos. 5, 6, 7 and 10.

The greater the quantity of peptides added the more a lowering of measured activity is observed.

EXAMPLE 9

The effect of immunogenic peptides according to the invention

Four batches of five mice were chosen to receive the peptides SI Nos. 1, 2, 6, 10 respectively.

The peptides prepared as described in Example 2 were injected on days 0, 30, 60 in a quantity of 15 µg per injection. On day 70 the mice were sacrificed, their T-cells were isolated (spleen and ganglia) and their serum was stored.

CMI, ELISA and Western blot tests were carried out:

In the CMI test, killer cells were in evidence in vitro after stimulation by the immunizing peptide but not after stimulation by the other peptides (measured by the release or chromium 21 test).

In the ELISA test (plates marked with the different peptides) the serums showed a positivity for the plates marked with the immunizing peptide, and this, at very high dilutions (of the order of 1 to 750).

In the Western blot test (Abott HIV-1 detection kit), the gp160 and gp120 bands showed a signal for the peptides SI Nos. 1, 6, 10 and gp160 and gp41 for the peptide SI No. 2.

EXAMPLE 10

Immunogenicity of viruses depleted according to the invention.

HIV-1 viruses depleted with formalin were prepared as described in Example 5A. A quantity of 1 mg/ml is combined with calcium phosphate as described in Examples 3 and 9.

In the Western blot test (Abott detection kit), all the known standard bands are found again (gp160, gp121, p55, gp4l).

In the CMI test, after stimulation by the peptides (the HGP30 segment of gag p17, peptide SI No. 4 of gp41) or by the entire virus inactivated by heat, or also by pure gp160, a killer cell activity is found again, which is not observed in non-immunized mice.

EXAMPLE 11

Loss of infectious power of viruses depleted according to the invention.

1 mg of HIV-1 virus depleted as described in Example 5A was resuspended in 1 ml of RPMI 1640, FCS 10% and the whole is added to a pellet of 5 million cells sensitive to infection by HIV-1 (H9 and MT4 cells).

After incubation for two hours at 37° C. the cells are washed twice in RPMI and put back in culture under standard conditions. The DNA of these cells was removed after 3 days and after 8 days and a PCR amplification is carried out (Polymerase Chain Reaction or enzymatic amplification) with several primers in gag (SK17, SK18), pol, env. These tests (capable of locating three copies of integrated DNA) carried out several times always proved negative.

In the same way, a PCR test carried out after a reverse transcription stage performed directly on 1 mg of depleted virus gave an absence of signal which shows an absence of viral genome in the depleted virus (treated with 0.3N potassium hydroxide, incubated for two hours at 37° C. and neutralized with hydrochloric acid, but not treated with formalin).

Sequence identifier Nos. 1a and 1b

1a. Peptide having a sequence identical to that of the region of the P7 sub-unit of the gag protein of the HIV-1 virus sub-strain HXB2, ranging from the amino acid in position 377 to the amino acid in position 432*.

```
    Ile-Ala-Arg-Asn-Cys-Arg-Ala-Pro-Arg-Lys-Lys-Gly (SEQ ID NO:1).

1b. Phe-Leu-Leu-Ala-Val-Phe-Cys-Ile-Ala-Arg-Asn-Cys-Arg-Ala-Pro-Arg-Lys-Lys-Gly (SEQ ID NO:2).
```

20 μl of the suspension prepared in this way is injected by intramuscular route in five mice on days D 0, +30, +60. On day +70 the serum and the T-cells (spleen) of the mice are removed.

In the ELISA test (Abott detection kit), a positive response is found even at high dilutions of serum.

Sequence identifier Nos. 2a and 2b

2a. Peptide having a sequence identical to that of the region of the gp4l sub-unit of the env protein of the HIV-1 virus sub-strain HXB2, ranging from the amino acid in position 735 to the amino acid in position 753*.

```
    Asp-Arg-Pro-Glu-Gly-Ile-Glu-Glu-Glu-Gly-Gly-Glu-Arg-Asp-Arg-Asp-Arg-Ser (SEQ ID NO:3).

2b. Phe-Leu-Leu-Ala-Val-Phe-Cys-Asp-Arg-Pro-Glu-Gly-Ile-Glu-
```

```
    Glu-Glu-Gly-Gly-Glu-Arg-Asp-Arg-Asp-Arg-Ser (SEQ ID NO:4)
```

Sequence identifier Nos. 3a and 3b

3a. Peptide having a sequence identical to that of the region of the gp41 sub-unit of the env protein of the HIV-1 virus sub-strain HXB2, ranging from the amino acid in position 834 to the amino acid in position 857*.

gag protein of HIV-1, and unique to these two molecules among all the known proteins. It corresponds to residues 454–459 of the gag protein of HIV-1 and to residues 153–158 of the CD5 receptor.

```
    Glu-Gly-Thr-Asp-Arg-Val-Ile-Glu-Val-Val-Gln-Arg-Ala-Phe-

Arg-Ala-Ile-Leu-His-Ile-Pro-Arg-Arg-Ile-Arg-Gln (SEQ ID NO:5).

3b. Phe-Leu-Leu-Ala-Val-Phe-Cys-Glu-Gly-Thr-Asp-Arg-Val-Ile-

Glu-Val-Val-Gln-Arg-Ala-Phe-Arg-Ala-Ile-Leu-His-Ile-Pro-

Arg-Arg-Ile-Arg-Gln (SEQ ID NO:6)
```

Sequence identifier No. 4
Peptide having a sequence identical to that of the region of the p15E sub-unit of the gag protein of the HIV-1 virus.
Leu-Gln-Asn-Arg-Arg-Gly-Leu-Asp-Leu-Leu (SEQ ID NO:7).

```
    Asn-Phe-Leu-Gln-Ser-Arg-Pro-Glu-Pro-Thr-Ala-Pro-Pro-Glu-Glu (SEQ ID NO:11).
```

Sequence identifier No. 5
Peptide having a sequence identical to that of the region of the gp41 sub-unit of the env protein of the HIV-1 virus sub-strain HXB2, ranging from the amino acid in position 560 to the amino acid in position 600*.

Sequence identifier No. 9

The peptide Thr-Thr-Leu-Phe-Cys-Ala (SEQ ID NO:18) (residues 20 to 25) of the env protein of HIV-1 has a very strong homology with the peptide Thr-Thr-Leu-Phe-Cys-

```
Cys-Gln-His-Leu-Leu-Gln-Leu-Thr-Val-Trp-Gly-Ile-Lys-Glu or Gln-Leu-Glu ou

Gln-Ala-Arg-Ile-Leu-Ala-Val-Glu-Arg-Tyr-Leu-Lys-Asp-Gln (SEQ ID NO:8).
```

Sequence identifier No. 6
The peptide Ser-Leu-Trp-Asp-Gln (amino acid residues 6–10 of SEQ ID NO:9) originating from the env protein of HIV-1 is totally identical (residues 110 to 114) to a segment of CD4 (residues 60 to 64).
His-Glu-Asp-Ile-Ile-Ser-Leu-Trp-Asp-Gln-Ser-Leu-Lys (SEQ ID NO:9).

Sequence identifier No. 7
The peptide Cys-Thr-Ala-Ser-Gln-Lys (SEQ ID NO:17) of the CD4 molecule (residues 16–21) shares a strong homology with the env protein of HIV-1 Cys-Ser-Ala-Thr-Glu-Lys, residues 28 to 33 and corresponding to amino acid residues 1–6 of SEQ ID NO:10).
Cys-Ser-Ala-Thr-Glu-Lys-Leu-Trp-Val-Thr-Val-Tyr-Tyr (SEQ ID NO:10)

Sequence identifier No. 8
The peptide Glu-Pro-Thr-Ala-Pro-Pro (amino acid residues 8–13 of SEQ ID NO:11) is common between CD5 and the Leu (amino acid residues 4–9 of SEQ ID NO:12) of TNF-α (residues 45 to 50).
Ala-Gly-Ala-Thr-Thr-Leu-Phe-Cys-Leu-Leu-His (SEQ ID NO:12).

Sequence identifier No. 10
The peptide Leu-Leu-Leu-Asn-Gly-Ser-Leu-Ala (amino acid residues 2–9 of SEQ ID NO:13) of the env protein of HIV-1 (residues 259–267) possesses a significant similarity with the following immunoregulatory molecules: HLA of class I (residues 11–18), β chain of T-cell receptor (residues 14 to 21), and G-CSF (residues 17 to 24).
Gln-Leu-Leu-Leu-Asn-Gly-Ser-Leu-Ala-Glu-Glu-Glu (SEQ ID NO:13).

Sequence identifier No. 11
The peptide Gln-Leu-Thr-Val-Trp (amino acid residues 5–9 of SEQ ID NO:14) is common to the env protein of HIV-1 (residues 566–570) and to the α chain of the T-cell receptor (residues 130–134).

Gln-His-Leu-Leu-Gln-Leu-Thr-Val-Trp-Gly-Ile-Lys (SEQ ID NO:14).

Sequence identifier No. 12

The peptide Gly-Ile-Arg-Pro-Val-Val (amino acid residues 2–7 of SEQ ID NO:15) of the env protein of HIV-1 (residues 250–256) has a very strong homology with the peptide Gly-Ile-Arg-Lys-Val-Val (SEQ ID NO:19) of the α chain of the precursor of the leukocyte adhesion protein (residues 230–236).

His-Gly-Ile-Arg-Pro-Val-Val-Ser-Thr-Gln (SEQ ID NO:15).

* : Numeration by Myers et al, retroviruses and AIDS (1990) Theoretical Biology and Biophysics, Los Alamos Labs., Los Alamos NM 87745 USA, Ed. Myers et al ; this numeration varies slightly according to the HIV strain chosen.

We claim:

1. A method for reducing the titer of a circulating native cytokine which is overproduced in a pathological condition comprising immunizing a subject in need thereof with an immunogenic composition comprising a biologically inactive analog or fragment of said native cytokine or a physically- or chemically-treated, biologically inactivated cytokine, in an amount sufficient to induce an immune response specific to said native cytokine wherein said immune response results in the reduction of the circulating titer of said native cytokine.

2. The method in accordance with claim 1, wherein said subject is immunized with an immunogenic composition comprising said biologically inactive fragment of said native cytokine.

3. The method in accordance with claim 1, wherein said subject is immunized with an immunogenic composition comprising said biologically inactive analog of said native cytokine.

4. The method in accordance with claim 1, wherein said subject is immunized with an immunogenic composition comprising said physically- or chemically-treated, biologically inactivated cytokine.

5. The method in accordance with claim 1, wherein said immunogenic composition further comprises an immunogen selected from the group consisting of an inactivated bacterial agent, an inactivated viral agent, a sub-unit bacterial immunogen, a sub-unit viral immunogen, and a tumor immunogen.

6. The method in accordance with claim 1, wherein said circulating native cytokine is interleukin-6 (IL-6), said pathological condition is a malignant tumor associated with the overproduction of IL-6, and said physically- or chemically-treated, biologically inactivated cytokine is IL-6.

7. The method in accordance with claim 1, wherein said malignant tumor is a multiple myeloma.

8. The method in accordance with claim 1, wherein said circulating native cytokine is interleukin-4 (IL-4) or interleukin-5 (IL-5), said pathological condition is an autoimmune disease or an allergy associated with the overproduction of IL-4 or IL-5, and said physically- or chemically-treated, biologically inactivated cytokine is IL-4 or IL-5.

9. The method in accordance with claim wherein said circulating native cytokine is interferon-α (IFN-α), said pathological condition is associated with human immunodeficiency virus (HIV) infection and the overproduction of IFN-α, and said physically- or chemically-treated, biologically inactivated cytokine is IFN-α.

10. The method in accordance with claim 9, wherein said immunogenic composition further comprises sub-unit HIV immunogens selected from the group consisting of gag peptides and env peptides.

11. The method in accordance with claim 10, wherein said sub-unit HIV immunogens are selected from the group of peptides having the amino acid sequences set forth in SEQ ID NO; 1, SEQ ID NO: 3, SEQ ID NO: 5, SEQ ID NO: 7, SEQ ID NO: 8, SEQ ID NO: 9, SEQ ID NO:10, SEQ ID NO:11, SEQ ID NO:13, SEQ ID NO:14, and mixtures thereof.

12. The method in accordance with claim 10, wherein said immunogenic composition further comprises a mixture of sub-unit HIV immunogens having the amino acid sequence set forth in SEQ ID NO:2, SEQ ID NO:4, SEQ ID NO:6 and SEQ ID NO:8.

* * * * *

```
                          SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
           (A) LENGTH: 12 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 1:

Ile Ala Arg Asn Cys Arg Ala Pro Arg Lys Lys Gly
   1               5                   10

(2) INFORMATION FOR SEQ ID NO: 2:

(i) SEQUENCE CHARACTERISTICS:
           (A) LENGTH: 19 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 2:

Phe Leu Leu Ala Val Phe Cys Ile Ala Arg Asn Cys Arg Ala Pro Arg
   1               5                   10                  15

Lys Lys Gly (2) INFORMATION FOR SEQ ID NO: 3:

(i) SEQUENCE CHARACTERISTICS:
           (A) LENGTH: 18 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 3:

Asp Arg Pro Glu Gly Ile Glu Glu Glu Gly Gly Glu Arg Asp Arg Asp
   1               5                   10                  15

Arg Ser (2) INFORMATION FOR SEQ ID NO: 4:

(i) SEQUENCE CHARACTERISTICS:
           (A) LENGTH: 25 amino acids
           (B) TYPE: amino acid
           (C) STRANDEDNESS: single
           (D) TOPOLOGY: linear
```

(ii) MOLECULE TYPE: peptide (xi) SEQUENCE DESCRIPTION: SEQ ID NO: 4:

Phe Leu Leu Ala Val Phe Cys Asp Arg Pro Glu Gly Ile Glu Glu
1               5                   10                  15

Gly Gly Glu Arg Asp Arg Asp Arg Ser
            20                  25

(2) INFORMATION FOR SEQ ID NO: 5:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 5:

Glu Gly Thr Asp Arg Val Ile Glu Val Val Gln Arg Ala Phe Arg Ala
1               5                   10                  15

Ile Leu His Ile Pro Arg Arg Ile Arg Gln
            20                  25

(2) INFORMATION FOR SEQ ID NO: 6:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 6:

Phe Leu Leu Ala Val Phe Cys Glu Gly Thr Asp Arg Val Ile Glu Val
1               5                   10                  15

Val Gln Arg Ala Phe Arg Ala Ile Leu His Ile Pro Arg Arg Ile Arg
            20                  25                  30

Gln (2) INFORMATION FOR SEQ ID NO: 7:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 7:

Leu Gln Asn Arg Arg Gly Leu Asp Leu Leu
1               5                   10

(2) INFORMATION FOR SEQ ID NO: 8:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 8:

```
Cys Gln His Leu Leu Gln Leu Thr Val Trp Gly Ile Leu Glx Leu Glx
1               5                   10                  15

Ala Arg Ile Leu Ala Val Glu Arg Tyr Leu Lys Asp Gln
            20                  25
```

(2) INFORMATION FOR SEQ ID NO: 9:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

```
His Glu Asp Ile Ile Ser Leu Trp Asp Gln Ser Leu Lys
1               5                   10
```

(2) INFORMATION FOR SEQ ID NO: 10:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Cys Ser Ala Thr Glu Lys Leu Trp Val Thr Val Tyr Tyr
1               5                   10
```

(2) INFORMATION FOR SEQ ID NO: 11:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Asn Phe Leu Gln Ser Arg Pro Glu Pro Thr Ala Pro Pro Glu Glu
1               5                   10                  15
```

(2) INFORMATION FOR SEQ ID NO: 12:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Ala Gly Ala Thr Thr Leu Phe Cys Leu Leu His
1               5                   10
```

(2) INFORMATION FOR SEQ ID NO: 13:

(i) SEQUENCE CHARACTERISTICS:
        (A) LENGTH: 12 amino acids
        (B) TYPE: amino acid
        (C) STRANDEDNESS: single
        (D) TOPOLOGY: linear

```
       (ii) MOLECULE TYPE: peptide (xi) SEQUENCE DESCRIPTION: SEQ ID NO: 13:

Gln Leu Leu Leu Asn Gly Ser Leu Ala Glu Glu Glu
1               5                   10

(2) INFORMATION FOR SEQ ID NO: 14:

(i) SEQUENCE CHARACTERISTICS:
           (A) LENGTH: 12 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 14:

Gln His Leu Leu Gln Leu Thr Val Trp Gly Ile Lys
1               5                   10

(2) INFORMATION FOR SEQ ID NO: 15:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO: 15:

His Gly Ile Arg Pro Val Val Ser Thr Gln
1               5                   10

(2) INFORMATION FOR SEQ ID NO:16:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:16:

Leu Glu Arg Ile Leu Leu
1               5

(2) INFORMATION FOR SEQ ID NO:17:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:17:

Cys Thr Ala Ser Gln Lys
1               5

(2) INFORMATION FOR SEQ ID NO:18:

(i) SEQUENCE CHARACTERISTICS:
           (A) LENGTH: 6 amino acids
           (B) TYPE: amino acid
           (C) STRANDEDNESS: single
           (D) TOPOLOGY: linear
```

```
    (ii) MOLECULE TYPE: peptide (xi) SEQUENCE DESCRIPTION: SEQ ID NO:18:

Thr Thr Leu Phe Cys Ala
1               5

(2) INFORMATION FOR SEQ ID NO:19:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:19:

Gly Ile Arg Lys Val Val
1               5
```